(12) United States Patent
Nolan et al.

(10) Patent No.: US 11,833,145 B2
(45) Date of Patent: Dec. 5, 2023

(54) NICOTINE FORMULATION

(71) Applicant: YATZZ LIMITED, Carlow (IE)

(72) Inventors: Christopher Nolan, Carlow (IE); Joseph Kavanagh, Carlow (IE); Kieran Raleigh, Carlow (IE); Brian O'Rourke, Carlow (IE)

(*) Notice: Subject to any disclaimer, the term of this patent is extended or adjusted under 35 U.S.C. 154(b) by 191 days.

(21) Appl. No.: 17/057,700

(22) PCT Filed: May 31, 2019

(86) PCT No.: PCT/EP2019/064212
§ 371 (c)(1),
(2) Date: Nov. 23, 2020

(87) PCT Pub. No.: WO2019/229249
PCT Pub. Date: Dec. 5, 2019

(65) Prior Publication Data
US 2021/0196700 A1    Jul. 1, 2021

(30) Foreign Application Priority Data
Jun. 1, 2018 (EP) .................................... 18175640

(51) Int. Cl.
| A61K 31/465 | (2006.01) |
| A61K 9/00 | (2006.01) |
| A61K 47/12 | (2006.01) |
| A24B 15/167 | (2020.01) |
| A61M 15/00 | (2006.01) |
| A61M 15/06 | (2006.01) |

(52) U.S. Cl.
CPC .......... *A61K 31/465* (2013.01); *A24B 15/167* (2016.11); *A61K 9/0078* (2013.01); *A61K 47/12* (2013.01); *A61M 15/0085* (2013.01); *A61M 15/06* (2013.01)

(58) Field of Classification Search
CPC .... A24B 15/167; A61K 31/465; A61K 47/12; A61K 9/0078; A61M 15/0085; A61M 15/06
See application file for complete search history.

(56) References Cited

U.S. PATENT DOCUMENTS

| 9,215,895 B2* | 12/2015 | Bowen | A61P 43/00 |
| 2004/0034068 A1 | 2/2004 | Warchol | |
| 2010/0236562 A1* | 9/2010 | Hearn | A61P 25/34 |
| | | | 131/330 |
| 2015/0020823 A1* | 1/2015 | Lipowicz | A24F 40/42 |
| | | | 131/359 |

FOREIGN PATENT DOCUMENTS

| DE | 10 2015 117811 A1 | 4/2017 |
| GB | 2 133 691 A | 8/1984 |

OTHER PUBLICATIONS

ISR; European Patent Office; NL; Aug. 30, 2019.

\* cited by examiner

*Primary Examiner* — Kara R McMillian
(74) *Attorney, Agent, or Firm* — Patshegen IP; Moshe Pinchas

(57) ABSTRACT

The invention relates to a pharmaceutical formulation comprising nicotine. The formulation can be aerosolised at ambient temperature for delivery via inhalation. The invention also relates to a method of delivering nicotine to a subject via inhalation, and specifically via the use of a nebuliser.

13 Claims, 1 Drawing Sheet

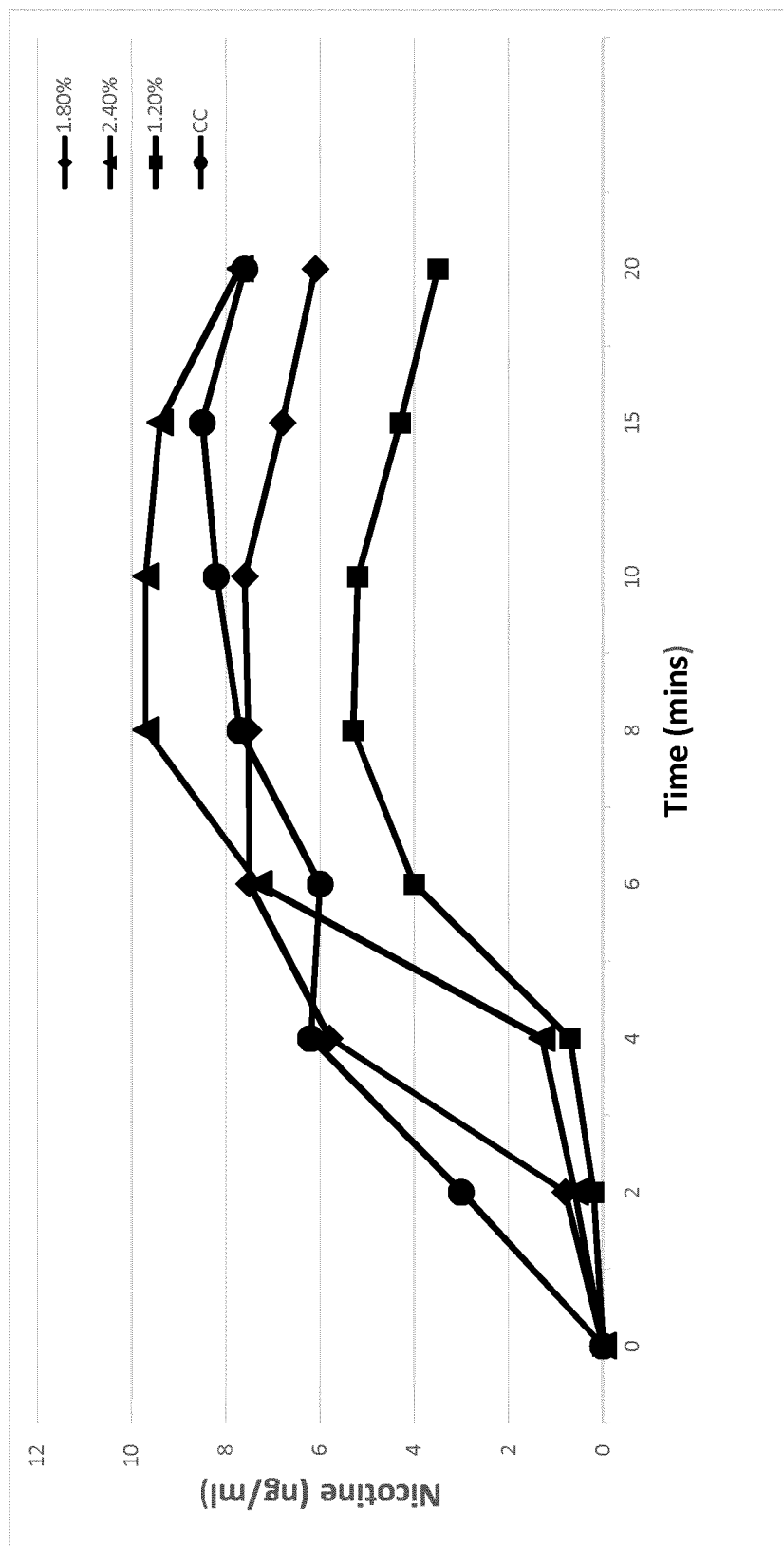

NICOTINE FORMULATION

TECHNICAL FIELD

The present invention relates to a pharmaceutical formulation comprising nicotine and a high volume of water. The formulation can be aerosolised at ambient temperature for delivery via inhalation. The invention also relates to a method of delivering nicotine to a subject via inhalation, and specifically via the use of a nebuliser. In alternative embodiments, the formulation can be delivered via a conventional e-cigarette device.

BACKGROUND

The serious health risks associated with smoking have been well documented. It is estimated that smoking tobacco, which comprises the alkaloid nicotine, is responsible for over seven million premature deaths a year (World Health Organisation), making it one of the leading causes of preventable death. Smoking also leads to diseases such as stenosis, lung cancer, and chronic obstructive pulmonary disease, while smoking during pregnancy can lead to miscarriage, premature birth, stillbirth and low birth weight and is reported to increase the risk of cot death by at least 25% (https://www.nhs.uk/smokefree/why-quit/smoking-health-problems). Second-hand smoke, or passive smoking, causes more than 890 000 premature deaths per year, many of them among children. However, it is not the nicotine itself that is primarily harmful to health, but the by-products of tobacco smoke.

Nicotine replacement therapies (NRTs) are pharmaceutical therapies which administer nicotine by means other than smoking tobacco, while allowing a user to mimic the effect of cigarette smoking. NRTs are associated with increased success at smoking cessation compared with placebos (Silagy et al. "Nicotine replacement therapy for smoking cessation", Cochrane Database of Systematic Reviews 2004; (3):CD000146). NRTs typically include transdermal patches, gums, oral and nasal sprays, inhalers, tablets and lozenges. However, NRTs suffer from a number of disadvantages, and primarily from inferior nicotine pharmacokinetic (PK) profiles when compared with combustible cigarettes (CCs).

Electronic cigarettes, or e-cigarettes, are handheld devices, often made to look like conventional CCs, and can be used by smokers to mimic the smoking action. E-cigarettes typically comprise a mouthpiece, a cartridge, an atomiser, a microprocessor, and a battery. The cartridge contains an e-liquid, which comprises the nicotine in viscous solvents such as vegetable glycerine and propylene glycol. The e-liquid is heated to high temperatures in the e-cigarette to form a vapour, which is inhaled by the user. The global use of e-cigarettes has increased exponentially since their introduction into consumer markets in 2004, with estimated global sales of US$7 billion annually (World Health Organisation, Backgrounder on WHO report on regulation of e-cigarettes and similar products). However, known e-cigarettes often do not provide a PK profile comparable to that of CCs, and as such do not reduce the urge to smoke for many users.

In addition, smoking of both conventional CCs and e-cigarettes involves heating of the nicotine formulation in order to combust or vaporise the ingredients for inhalation. This heating results in the generation of undesirable by-products which are known to have an adverse effect on health. While the majority of toxic chemicals found in tobacco smoke from conventional CCs are absent in e-cigarette vapour, e-cigarettes still generate toxicants and traces of heavy metals (Hajek et al. Addiction. 2014 November; 109(11): 1801-1810). In addition, e-cigarette vapour can be inhaled passively by third parties.

It is an aim of the invention to obviate or mitigate one or more of the disadvantages associated with the prior art. Ideally, it would be advantageous to provide a nicotine formulation which exhibits a similar PK profile to a CC. A formulation which could be administered at ambient temperatures would also be advantageous, as would be its mode of delivery. A reduction in the formation of deleterious side-products would also be beneficial, whether administered at ambient or conventional e-cigarette temperatures, as would a reduction in the vapour cloud generated.

SUMMARY OF THE INVENTION

According to an aspect of the invention there is provided a pharmaceutical formulation comprising 0.1-8% wt. % of nicotine; at least 65 wt. % water; and one or more of flavouring agents, co-solubilisers and solubilisers; wherein the nicotine is the form of a nicotine salt of nicotine and an acid; and wherein the pharmaceutical formulation has an acidic pH. The formulation may be an inhalable pharmaceutical formulation.

According to another aspect of the invention there is provided a method of delivering nicotine to a subject, comprising providing an aerosolised formulation comprising 0.1-8% wt % of nicotine and at least 65 wt. % water; and administering the aerosolised formulation via inhalation. The method may comprise providing the formulation as a liquid and nebulizing the liquid formulation to form an aerosolised formulation for inhalation.

Various further features and aspects of the invention are defined in the claims.

BRIEF DESCRIPTION OF THE DRAWINGS

Embodiments of the present invention will now be described by way of example only with reference to the accompanying drawings where like parts are provided with corresponding reference numerals and in which:

FIG. 1 shows venous blood plasma concentrations of nicotine pre- and post-inhalation of a formulation according to the invention.

DETAILED DESCRIPTION

The present invention relates to a pharmaceutical formulation comprising 0.1-8% wt % of nicotine; at least 65 wt. % water; and one or more of flavouring agents, co-solubilisers and solubilisers. The nicotine is included in the formulation in the form of a salt of nicotine and an acid, or salts of nicotine and an acid. The pharmaceutical formulation has an acidic pH.

Advantageously, the formulation comprises high volumes of water. This results in a decrease in the amount of deleterious side-products produced when the formulation is aerosolised, and subsequently inhaled by a subject. In addition, it advantageously appears that the high volumes of water in the formulation lead to improved PK behaviour, with PK curves of the formulations according to the invention demonstrating correlation with those of CCs. A high water content also facilitates aerosol production. In an embodiment, the formulation comprises at least 70 wt. % of water. In another embodiment, the formulation comprises at least 75 wt. % of water, or at least 80 wt. % of water.

Typical formulations for e-cigarettes comprise large volumes (~>60%) of viscous chemicals such as glycerine and propylene glycol. Heating to high temperatures is required to volatilize these components for administration, resulting in the generation of harmful by-products. In the formulation of the present invention, however, low quantities of such viscous chemicals are used. Specifically, the formulation of the present invention does not comprise viscous chemicals such as glycerine and propylene glycol in large quantities. In an embodiment, the formulation comprises less than 20%, and preferably less than 15% in total of propylene glycol and glycerine.

Other known formulations comprise ingredients such as hydrofluorocarbons (HFCs), which are used in respiratory drug delivery. However, despite their relative widespread use as propellants, HFCs are known to have adverse effects on the stratospheric ozone layer, and there are concerns surrounding their potential neurotoxicity (Ritchie G D et al., Acute neurobehavioral effects in rats from exposure to HFC 134a or CFC 12; Neurotoxicology 22(2): 2001; pp. 233-248).

Advantageously, the high volumes of water in the formulation according to the invention mitigate the need to heat the formulation to high temperatures for inhalation, resulting in a decrease in harmful by-products. The formulation also avoids the use of HFCs, with their associated disadvantages. In an embodiment, the formulation of the invention does not comprise hydrofluorocarbons.

According to the invention, the nicotine is included in the formulation at a concentration of from 0.1 to 8 weight %. Ideally, the formulation can comprise varying amounts of nicotine to assist in smoking reduction or cessation in a user. In embodiments, the nicotine is included in the formulation at a concentration of from 0.1 to 5% of nicotine, or from 0.1 to 3% of nicotine. Within this range, formulations comprising from 0.3-0.6%, from 1-1.2%, from 1.6-1.9% and from 2.1-2.5% may be preferred.

Nicotine (3-(1-methyl-2-pyrrolidinyl)-pyridine) may be naturally-occurring nicotine, or may be a synthetic nicotine.

In the formulation the nicotine is included in the form of a salt. The lower pH of the nicotine salt versus free base nicotine attenuates the irritating effect of the nicotine and results in a more palatable formulation. A single salt or a mixture of nicotine salts may be used. Suitable acids for forming the nicotine salt must exhibit minimal or no toxicity to humans.

Many suitable acids have poor solubility in water, but yield a soluble salt when mixed with the alkaline nicotine. When such poorly soluble acids are used, stoichiometric amounts of the acid are mixed with the nicotine to form a soluble product, before a water soluble acid is added to adjust the pH.

In an embodiment, the acid is selected from acetic acid, acetylsalicylic acid, alginic acid, 2-aminoethanesulfonic acid (taurine), aminomethylphosphonic acid, arachidic acid, ascorbic acid, aspartic acid, azelaic acid, barbituric acid, benzylic acid, benzoic acid, butanoic acid, butyric acid, capric acid, caproic acid, caprylic acid, carbonic acid, cinnamic acid, citric acid, decanoic acid, dodecanoic acid, enanthic acid, ethanoic acid, folic acid, formic acid, fumaric acid, gallic acid, gentisic acid, gluconic acid, glutamic acid, glutaric acid, heptanoic acid, hexanoic acid, hydrochloric acid, icosanoic acid, ketobutyric acid, lactic acid, lauric acid, levulinic acid, malic acid, maleic acid, malonic acid, margaric acid, methanoic acid, 2-methylbutyric acid, 3-methylbutyric acid, 2-methyl propanoic acid, 3,7-dimethyl-6-octenoic acid (citronellic acid), myristic acid, nonadecanoic acid, octanoic acid, oleic acid, oxalic acid, 2-oxobutyric acid, palmitic acid, pectic acid, pelargonic acid, pentadecanoic acid, pentanoic acid, phthalic acid, phenylacetic acid, picric acid, propanoic acid, propiolic acid, pyruvic acid, rosolic acid, salicyclic acid, sorbic acid, stearic acid, succinic acid, sulfosalicylic acid, tannic acid, tartaric acid, tetradecanoic acid, p-toluenesulfonic acid, tridecanoic acid, tridecylic acid, trifluoromethanesulfonic acid, undecanoic acid, undecylic acid, uric acid and valeric acid In an embodiment, the acid is selected from lactic acid, acetylsalicylic acid, 2-aminoethanesulfonic acid (taurine), aminomethylphosphonic acid, arachidic acid, ascorbic acid, azelaic acid, barbituric acid, benzylic acid, butanoic acid, capric acid, caproic acid, caprylic acid, carbonic acid, cinnamic acid, decanoic acid, dodecanoic acid, enanthic acid, ethanoic acid, folic acid, fumaric acid, gluconic acid, glutaric acid, heptanoic acid, hexanoic acid, icosanoic acid, ketobutyric acid, levulinic acid, maleic acid, malonic acid, margaric acid, methanoic acid, 2-methylpropanoic acid (isobutyric acid), 3,7-dimethyl-6-octenoic acid (citronellic acid), myristic acid, nonadecanoic acid, nonadeclylic acid, octadecanoic acid, octanoic acid, oleic acid, 2-oxobutyric acid, pelargonic acid, pentadecanoic acid, pentadecylic acid, pentanoic acid, propanoic acid, propiolic acid, rosolic acid, sorbic acid, stearic acid and succinic acid, tetradecanoic acid, p-toluenesulfonic acid, tridecanoic acid, tridecylic acid, trifluoroacetic acid, trifluoromethanesulfonic acid, undecanoic acid, undecylic acid and uric acid.

In an embodiment, the acid is lactic acid. Lactic acid is a naturally-occurring organic acid and is native to the human body, making it suitable for use in the pharmaceutical formulation of the invention.

In an alternative embodiment, the acid is 2-methylpropanoic acid (isobutyric acid). Isobutyric acid imparts a dairy/cheesy flavoured note to the formulation, thereby improving palatability and therefore isobutyric acid, along with butyric acid which has a similar effect, is particularly suitable for use in the present invention.

In an alternative embodiment, the acid is benzoic acid.

The pharmaceutical formulation has an acidic pH. Advantageously, when the formulation has an acidic pH, nicotine can be readily absorbed into the lungs.

In an embodiment, the formulation has a pH of from 4.5 to 6.5.

In an embodiment, the formulation has a pH of from 4.5 to 5.9.

In an embodiment, the formulation has a pH of from 5.0 to 5.8.

The pH of the formulation is typically adjusted as required using an excess of the acid used to form the nicotine salt. When a poorly soluble acid is used to form the salt, another, water-soluble acid may be used to adjust the pH.

In an embodiment, the formulation does not include a separate buffering agent or pH regulating agent.

In an embodiment, the formulation comprises at least 75% of water. In an embodiment, the formulation comprises at least 77% of water. As noted above, high volumes of water can facilitate aerosol production and lead to improved PK characteristics. The formulation also leads to little or no observable vapour "cloud" being produced when the product is exhaled, lessening the impact of passive smoking on third parties.

In an embodiment, the formulation is a liquid formulation. In an embodiment, the formulation is provided as a liquid formulation. For instance, the liquid formulation can be provided in a cartridge, for use with an aerosolising or nebulizing device such as an e-cigarette, nebulizer or metered-dose inhaler [MDI].

In an embodiment, the formulation is in the form of aerosolised droplets.

Mass Median Aerodynamic Diameter (MMAD) refers to the diameter at which 50% of the particles by mass are larger, and 50% of the particles by mass are smaller. The size of the droplets determines the site of deposition of the particles in the respiratory tract. In an embodiment, the aerosolised droplets may have an MMAD of from 1 to 6 μm. In an embodiment, the aerosolised droplets may have an MMAD of from 2 to 4 μm. When the MMAD is within these ranges, the aerosolised droplets are small enough to avoid irritating the back of the throat, but large enough to settle in terminal bronchi and alveoli rather than simply being exhaled, facilitating deep lung delivery. Advantageously, the high volume of water in the formulation of the invention facilitates the formation of such small droplets, and consequently delivery to the deep lung. This deep lung delivery can lead to a sense of smoking satisfaction in users.

In an embodiment, the formulation comprises one or more flavouring agents. The flavouring agent may be a natural flavouring agent or an artificial or simulated flavouring agent, and combinations of flavouring agents can be used. Suitable flavouring agents for use in nicotine-containing products are known in the art. Examples of suitable flavouring agents include fruit flavours such as apple, banana, bergamot, cherry, grape, lemon, orange, pear, pineapple, raspberry and strawberry; plant flavours such as vanilla, nut flavours such as hazelnut; spice flavours such as cinnamon and clove; root flavours such as ginger and liquorice, mint flavours such as menthol, eucalyptol and pinene; and tobacco flavours.

In an embodiment, the formulation comprises a tobacco, fruit or mint flavouring.

In an embodiment, the flavouring agent is a water-soluble flavouring agent. In an embodiment, the flavouring agent is selected from acetic acid, 2-acetylpyridine, 3-acetylpyridine, 2-acetyl-5-methylfuran, α-angelica Lactone (5-methyl-3H-furan-2-one), 4,5-dimethyl-3-hydroxy-2,5-dihydrofuran-2-one, 2,5-dimethylpyrazine, 2,6-dimethylpyrazine, ethyl acetate, 2-ethyl-3(5 or 6)-dimethylpyrazine, ethyl-3-hydroxybutyrate, 5-ethyl-3-hydroxy-4-methyl-2(5H)-furanone, 5-ethyl-4-hydroxy-2-methyl-3(2H)-furanone, ethyl maltol, 2-ethyl-3(5)-dimethylpyrazine, 2-ethyl-3(6)-dimethylpyrazine, furaneol, 4-hydroxy-2,5-dimethyl-3(2H)-furanone, 2-furanmethanethiol formate, furfural (2-Furaldehyde), furfuryl alcohol, furfuryl mercaptan, 2,3-hexanedione, Y-hexalactone, homo furaneol (4-hydroxy-5-ethyl-2-methyl-3(2H)-furanone), 4-hydroxybutanoic acid lactone, 4-hydroxy-2,5-dimethyl-3(2H)-furanone, 4-hydroxy-5-methyl-3-furanone, isobutyraldehyde, malic acid, maltol ((3-hydroxy-2-methyl-4H-pyran-4-one), methional (3-methylsulfanylpropanal), methyl acetate, methyl cyclopentenolone (3-methylcyclopentane-1,2-dione), methyl cyclopentenolone (hydrate), 5-methylfurfural, methyl nicotinate, 4-methyl-5-thiazoleethanol, neohesperidin dihydrochalcone, 2-oxobutyric acid, 4-oxoisophorone (2,6,6-trimethyl-2-cyclohexene-1,4-dione), propionaldehyde, pyruvaldehyde, triacetin, 2,6,6-trimethyl-2-cyclohexene-1,4-dione and 2,4,5-trimethylthiazol, 2,3,5-trimethyl pyrazine, vanillyl alcohol.

Alternatively, the flavouring agent may be a flavouring oil, such as a natural flavouring essential oil. Such oils include, but are not limited to ajwain oil, angelica root oil, anise oil, asafoetida, balsam of Peru, basil oil, bay oil (*Laurus nobilis*), bergamot oil, black pepper, buchu oil, cannabis flower essential oil, calamodin oil, caraway seed oil, cardamom seed oil, carrot seed oil, cedar oil, chamomile oil, cinnamon oil, citron oil, citronella oil, clary sage oil, coconut oil, clove oil, coffee oil, coriander oil, costmary oil, costus root oil, cranberry seed oil, cubeb oil, cumin seed oil, cypriol oil, curry leaf oil, dill oil, elecampane oil, eucalyptus oil, fennel seed oil, fenugreek oil, galangal oil, garlic oil, geranium oil, ginger oil, goldenrod oil, grapefruit oil, helichrysum oil, hickory nut oil, horseradish oil, hyssop, juniper berry oil, lavender oil, *ledum*, lemon oil, lemongrass, lime, limonene, linalool, mandarin, marjoram, melissa oil (lemon balm), *Mentha arvensis* oil, mountain savory, myrrh oil, myrtle, neroli, nutmeg oil, orange oil, oregano oil, orris oil, palo santo, parsley oil, peppermint oil, petitgrain, pine oil, ravensara, Roman chamomile, rose oil, rosehip oil, rosemary oil, sage oil, star anise, sassafras oil, schisandra oil, spearmint oil, spikenard, spruce oil, star anise oil, tangerine, tansy, tarragon oil, thyme oil, turmeric, valerian, wintergreen, yarrow oil and zedoary oil.

However, the flavouring agent is not particularly limited, and other suitable flavouring agents would be known to a person skilled in the art. In an embodiment, the formulation comprises one or more co-solubilisers. Suitable co-solubilisers include, but are not limited to propylene glycol, polyethylene glycol (PEG), glycerine, polyethylene glycol (PEG)/polypropylene glycol (PPG) co-polymers, polyvinylpyrrolidone, 1,2-hexanediol, 1,2-pentanediol, diethylene glycol mono-ethyl ether, dimethyl isosorbide, ethanol, n-butanol, n-pentanol; and mixtures thereof. In an embodiment, the co-solubiliser is propylene glycol, glycerine, or a mixture of propylene glycol and glycerine.

In an embodiment, the formulation comprises one or more solubilisers. Suitable solubilisers include, but are not limited to, polyoxyethylene (40) castor oil, poloxamer 407™ (poly(ethylene glycol)-block-poly(propylene glycol)-block-poly(ethylene glycol), polyoxyl (35) castor oil, polyoxyl (40) castor oil, polyoxyl (40) castor oil in admixture with PPG-1-PEG 9 lauryl glycol ether, PEG (40) castor oil, PPG-1-PEG 9 lauryl glycol ether, polyoxyethylated 12-hydroxystearic acid, PEG 300, PEG 400, dioleic acid PEG 600 ester, heptyl glucoside, isostearic acid monoisopropanolamide, coconut fatty acid diethanolamide, coconut fatty acid glycol ester, coconut fatty acid monoethanolamide, coconut fatty acid PEG200 ester, coconut fatty acid PEG600 ester, oleic acid PEG600 ester, oleic acid C12-C14 alkylester, oleic acid diethanolamide, oleic acid monoisopropanolamide, oleic acid PEG1000 ester, oleic acid PEG200 ester, rape seed oil diethanolamide, tall oil fatty acid diethanolamide, tall oil fatty acid monoisopropanolamide, tall oil PEG200 ester, tall oil PEG600 ester, polysorbate 20, polysorbate 40 (polyoxyethylene sorbitan monopalmitate/Tween™ 40), polysorbate 60, polysorbate 65, polysorbate 80 (Tween™ 80), polysorbate 85, sorbitan monolaurate, sorbitan monopalmitate, sorbitan monostearate, sorbitan monooleate, sorbitan monoisostearate, sorbitan tristearate; Cosmacol™ N119 (C12-C13 Pareth 9); and mixtures thereof.

In an alternative embodiment, suitable solubilisers include, but are not limited to, polyoxyethylene (40) castor oil, poloxamer 407™ (poly(ethylene glycol)-block-poly(propylene glycol)-block-poly(ethylene glycol), polyoxyl (35) castor oil, polyoxyl (40) castor oil, polyoxyl (40) castor oil in admixture with PPG-1-PEG 9 lauryl glycol ether, PEG (40) castor oil, PPG-1-PEG 9 lauryl glycol ether, polyoxyethylated 12-hydroxystearic acid, PEG 300, PEG 400, dioleic acid PEG 600 ester, heptyl glucoside, isostearic acid monoisopropanolamide, coconut fatty acid diethanolamide, coconut fatty acid glycol ester, coconut fatty acid monoethanolamide, coconut fatty acid PEG200 ester, coconut fatty acid PEG600 ester, oleic acid PEG600 ester, oleic acid C12-C14 alkylester, oleic acid diethanolamide, oleic acid monoisopropanolamide, oleic acid PEG1000 ester, oleic acid PEG200 ester, rape seed oil diethanolamide, tall oil fatty acid diethanolamide, tall oil fatty acid monoisopropanolamide, tall oil PEG200 ester, tall oil PEG600 ester, polysorbate 20, polysorbate 40 (polyoxyethylene sorbitan monopalmitate/Tween™ 40), polysorbate 60, polysorbate 65, polysorbate 85, sorbitan monolaurate, sorbitan monopalmitate, sorbitan monostearate, sorbitan monooleate, sorbitan monoisostearate, sorbitan tristearate; Cosmacol™ N119 (C12-C13 Pareth 9); and mixtures thereof.

In an embodiment, the solubiliser is PEG (40) hydrogenated castor oil.

In an embodiment, the formulation comprises one or more sweeteners. Suitable sweeteners include oxathiazinone sweeteners such as acesulfame and acesulfame K; dipeptide derivatives such as Alitame™, aspartame and aspartame derivatives and aspartame-like di- and tri-peptides such as neotame; sulfamates such as sodium cyclamate (sodium-N-cyclohexylsulfamate) and calcium cyclamate; sugar alcohols such as erythritol, xylitol, maltitol, mannitol, sorbitol, isomalt and tagatose; naturally occurring sweeteners such as xylose, glycyrrhizin and stevia; rare sugars such as d-psicose and d-allose; saccharin, sucralose, gluonic acid; and mixtures thereof.

In an embodiment, the formulation is an inhalable formulation.

By "inhalable formulation" is meant that the formulation is in the form of droplets suitable for inhalation by a subject. For instance, the MMAD of the droplets may be 12 μm or less, or the MMAD of the droplets may be 10 μm or less. In an embodiment, the MMAD is between 1 to 6 μm, or between 2 and 4 μm. The inhalable formulation can be obtained by aerosolising the liquid formulation previously described, for instance in a nebulizer.

Further ingredients such as suspending agents, thickening agents and/or excipients can be included in the formulation. The inclusion of such additional components would be within the remit of one skilled in the art.

In an embodiment, the pharmaceutical formulation comprises from 75 to 85 wt. % of water; from 0.1 to 8 wt. % of nicotine; from 0.1 to 15 wt. % of co-solubiliser; from 0.5 to 1.5 wt. % of sweetener; from 0.05 to 1.5 wt. % of flavouring; and from 1 to 5% of acid. In an embodiment, the nicotine is included at from 0.1 to 5%. In an embodiment, the acid is included at from 1 to 2%.

In an embodiment, the pharmaceutical formulation comprises from 75 to 85 wt. % water; from 0.1 to 8 wt. % nicotine; from 0.1 to 15 wt. % co-solubiliser; from 0.5 to 1.5 wt. % sweetener; and from 0.05 to 1.5 wt. % of flavouring. Preferably, the pharmaceutical formulation comprises >80 wt. % of water.

According to an aspect of the invention, there is provided a method of delivering nicotine to a subject, comprising providing an aerosolised formulation comprising 0.1-8% wt. % of nicotine and at least 65 wt. % water; and administering the aerosolised formulation via inhalation. The formulation may be the formulation described in detail above.

The method may further comprise providing the formulation in liquid form, and nebulising or aerosolising the liquid formulation to form the aerosolised formulation. For instance, the formulation may be supplied as a liquid, in a cartridge or similar, for use with a nebuliser. Accordingly, in an aspect of the invention there is provided a cartridge comprising the liquid formulation, and an e-cigarette or nebuliser device comprising the liquid formulation or a liquid-formulation-containing cartridge.

The liquid formulation may be nebulised via the application of oxygen, compressed air or ultrasonic power to form the aerosolised formulation. In an embodiment, the nebuliser is a mechanical nebuliser, a jet nebuliser, a mesh nebuliser such as a vibrating mesh nebuliser or an ultrasonic nebuliser such as a piezo or PZT nebuliser. In an embodiment, the nebuliser is a mesh nebuliser.

EXAMPLES

Methodology:

Viscosity was measured using a Cannon-Penske viscometer. The viscometer is first cleaned with deionized water followed by pure ethanol which is allowed to drain away, before the device is dried in a current of air. The viscometer is charged with the test-liquid by pouring it into the wider bored tube of the U-shaped apparatus until the large bulb reservoir is half-full. The viscometer is placed in a thermostatted bath and temperature allowed to equilibrate. The viscometer is carefully levelled, and the liquid drawn by pipette filler through the capillary of the narrower tube until the level reaches above a first fixed gradation mark. The pipette filler is carefully removed, and the liquid level allowed to fall to the first fixed gradation mark, at which point a stopwatch is activated. The time taken for the level to fall to a second, lower graduated mark is recorded. The procedure is repeated four additional times and the average time calculated.

The kinematic viscosity, ν, measured in $mm^2/s$, is calculated by multiplying the average time by the viscosity constant—which is supplied with each individual viscometer.

The invention will now be described with reference to the following non-limiting examples:

Example 1: Preparation of Formulation

A formulation comprising 0.3% (w/w) of nicotine was prepared as set out below. All non-nicotine ingredients used were of food-grade quality.

A stock solution of 5% w/w sucralose was prepared by adding 5.0 g of sucralose to 95.0 g of water. The mixture was stirred vigorously until a clear solution remained.

A flavour complex consisting of a mixture of 0.025 g of 5-ethyl-3-hydroxy-4-methyl-2(5H) furanone and 0.05 g of cis 3-hexen-1-ol was dissolved in propylene glycol sufficient to give 5 g of solution.

0.025 g of L-menthol was added to 1.0 g of Kolliphor™ RH-40 and the mixture was stirred until clear. This was added to the flavour complex along with 2.50 g of the 5% sucralose solution.

Separately, 0.30 g of nicotine was weighed into a beaker and dissolved in 90.67 g of water. 0.1 g of mannitol, followed by 0.1 g of sodium-N-cyclohexylsulphamate, was dissolved in the solution. The pH of the formulation was measured using a pH meter (Jenway 3510). 0.166 g of lactic acid was added to form a salt with nicotine (1:1 ratio). Excess lactic acid was then added dropwise until the pH of the solution reached 5.5.

The nicotine solution was added to the flavouring solution and the mixture stirred until homogeneous. A residual of 0.85 g of water was added.

Solutions comprising 0.6%, 1.2%, 1.8%, 2.4% and 5% (designated F #1 to F #5) of nicotine were prepared in the same manner.

The composition of the formulations is shown in Table 1 below:

TABLE 1

Nicotine formulations

| Component | F# 1 Wt. % | F#2 Wt. % | F#3 Wt. % | F#4 Wt. % | F#5 Wt. % |
|---|---|---|---|---|---|
| Water | 83.17 | 82.36 | 81.32 | 80.28 | 75.77 |
| Propylene glycol | 11.1 | 11.1 | 11.1 | 11.1 | 11.1 |
| PEG (40) hydrogenated castor oil | 0.50 | 0.50 | 0.50 | 0.50 | 0.50 |
| Flavouring | 1.10 | 1.10 | 1.10 | 1.10 | 1.10 |
| Glycerine | 2.10 | 2.10 | 2.10 | 2.10 | 2.10 |
| Stevia | 0.26 | 0.26 | 0.26 | 0.26 | 0.26 |
| Sucralose | 0.25 | 0.25 | 0.25 | 0.25 | 0.25 |
| Na N-cyclohexyl-sulphamate | 0.10 | 0.10 | 0.10 | 0.10 | 0.10 |
| Mannitol | 0.15 | 0.15 | 0.15 | 0.15 | 0.15 |
| Nicotine | 0.60 | 1.2 | 1.8 | 2.4 | 5.0 |
| Lactic acid | 0.67 | 0.88 | 1.32 | 1.76 | 3.67 |
| pH | 5.5 | 5.5 | 5.5 | 5.5 | 5.5 |

Example 2

A formulation was prepared according to the same methodology as Example 1, comprising the following:

TABLE 2

Nicotine formulation

| Component | Wt. % |
|---|---|
| Water | 80.45 |
| Nicotine | 3.6 |
| Lactic acid | 2.6 |
| Sucralose | 0.1 |
| Pyruvaldehyde | 1.0 |
| Glycerine | 12.25 |

The formulation had a pH of 5.

The viscosity of the formulation was then measured as follows:

The product, a red-brown liquid was evaluated for viscosity using the Cannon-Penske viscometer, supplied by PSL Rheotek, and its relative density determined using a 25 ml relative density bottle.

The formulation was found to have a kinematic viscosity of 1.866 $m^2/s \times 10^{-6}$ cS. Its relative density was 1.048 g/ml. Its dynamic viscosity was therefore 1.956 cP.

Pharmacokinetic Study:

Nicotine formulations comprising 1.2, 1.8 and 2.4% of nicotine were prepared as outlined above, with the concentrations chosen to encompass some of the doses likely to be acceptable to users.

4 Healthy volunteers (male & female) aged 18-55 years were eligible for the study if they had smoked manufactured cigarettes or vaped every day for the last year and typically smoked their first cigarette within 1 hour of waking.

All subjects were required to abstain from smoking for 12 hr prior to their scheduled dosing time. Participants were excluded if they had a known or suspected history of hypersensitivity to nicotine or any other component of the inhaler. Participants were also excluded if they had a history of confirmed chronic and/or serious pulmonary disease, including asthma, or chronic obstructive pulmonary disease, a history of myocardial infarction or cerebrovascular accident, other clinically significant cardiac or renal conditions, or any comorbidity that could place them at risk or interfere with the interpretation of the study data. Women who were breastfeeding were excluded from the study.

Participants were familiarized with the inhaler device using a placebo formulation on the day prior to receiving active treatment. The placebo formulation was identical to the active formulation described above, with the exception that the placebo formulation did not include nicotine.

The nicotine inhaler device used was a MicroBase™ Pocket AirNeb Mini Portable Nebuliser [Model No. MBPN002]. This device comprises a portable compact compressor with small delivery mouthpiece that allows a user to inhale. The average nebulization rate is >0.25 ml/min, and respirable output of MMAD 4 μm. Nicotine is delivered from each inhale, and level of nicotine is therefore dependent on an individual's depth of inhalation and number of "puffs" over the time span of 3 minutes+/−30 secs.

The device was filled with the formulations described above. Participants inhaled each time in a similar way to a cigarette. All participants were instructed to inhale at the same rate of one inhalation every 20 s+/−5 secs over approximately 3 min (i.e., approximately eight inhalations in total). This inhalation protocol should comprise a comparable inhalation to that of a CC for most users.

As a control, venous blood samples were collected 5 min pre-dose. Samples were then collected at 2, 4, 6, 8, 10, 15 and 20 minutes (+/−2 mins) post-dose (i.e., from the start of inhalation) for the measurement of plasma nicotine concentration by a liquid chromatography with tandem mass spectrometry method that was validated for linearity and precision.

The results of this study are shown in FIG. 1. The intervals vary slightly (i.e. +/−2 mins) due to human variation in obtaining the sample (i.e. the time to insert the needle etc.).

Venous plasma nicotine concentration post-inhalation of a CC is shown by (●). The CC profile shows a rapid increase in plasma nicotine levels over the first 8 minutes, reaching a plateau at about 20 minutes. The nicotine formulation of the invention showed a similar profile, particularly for the formulations comprising 1.8 and 2.4% of nicotine.

This data suggests that nicotine is rapidly entered into systemic circulation following inhalation of the formulation of the invention and exhibits a similar pharmacokinetic profile to CCs. This was borne out by the responses to the trial with users noting a high degree of satisfaction following inhalation of the formulation.

Users also visibly observed a lack of vapour cloud when exhaling the formulation of the invention.

Degradation Study:

Conventional e-cigarette liquids comprising viscous carriers such as propylene glycol and glycerine are suspected of generating trace levels of various toxins during vaporization. Tayyarah et al. (Reg. Toxicol. Pharmacol. 70 (2014): 704-710 determined the total carbonyls generated during vaporization for a series of commercial e-cigarette liquids. The carbonyls, including formaldehyde, acetaldehyde, acrolein, propionaldehyde, crotonaldehyde, methyl ethyl ketone and butyraldehyde, were typically found to be present at values between <0.05 to <0.09 mg per 99 puffs, indicating that although exposure is more limited than for conventional cigarettes, low levels of toxins are still present.

In order to determine degradation of the formulation of the present invention, the following composition was prepared and tested:

TABLE 3

Nicotine formulation for degradation testing

| Component | Wt. % |
|---|---|
| Water | 80.37 |
| Nicotine | 2.20 |
| Lactic acid | 1.70 |
| Sucralose | 0.13 |
| 4-hydroxy-5-methyl-furanone | 0.60 |
| Glycerine | 15.00 |

The formulation had a pH of 5.5.

The degradation study was carried out as follows:

The formulation of table 3 was analysed for known toxic compounds, and the results for this reference sample are shown below. The formulation was then vaporised using 1) a conventional heated e-cigarette device (which heats to 260° C.-280° C.); and 2) a portable nebulizer (Pocket Air® from Microbase Technology Corporation), in which the vapour is generated without heating, i.e. at ambient temperature. Volatile organic compounds (VOCs) present in the resulting formulation vapour were analysed by assaying a single 100 ml puff trapped in a suitable solid support containing 2,4-dinitrophenylhydrazine (DNPH) which was eluted and analysed by HPLC-DAD, using UV, RI and PDA detectors.

HPLC-DAD Conditions were as follows:
Column: C18 Atlantis
Temperature: 35° C.
Analysis Time: 10 min
Injection Vol: 20 µl
Detection: PDA, UV and RI
Eluent: 50:50 acetonitrile:water containing 0.1% triethylamine.

The results of the study are shown in Table 4 below:

TABLE 4

Results of degradation testing

| Compound | Reference Sample | Conventional e-cigarette heating | Ambient temperature |
|---|---|---|---|
| Nicotine | 2.21 ± 0.179 | 0.020 ± 0.002 | 0.022 ± 0.002 |
| Propylene Glycol | N.D.* | N.D.* | N.D.* |
| Glycerine | 10.05 ± 1.23 | 0.0012 ± 0.0001 | 0.001 ± 0.0001 |
| Diethylene Glycol | N.D.* | N.D.* | N.D.* |
| Ethylene Glycol | N.D.* | N.D.* | N.D.* |
| Acetone | N.D.* | N.D.* | N.D.* |
| Acetoin | N.D.* | N.D.* | N.D.* |
| Diacetyl | N.D.* | N.D.* | N.D.* |
| 2,3-Pentanedione (acetyl propionyl) | N.D.* | N.D.* | N.D.* |
| Propylene Oxide | N.D.* | N.D.* | N.D.* |
| Acrolein | N.D.* | N.D.* | N.D.* |
| Formaldehyde | N.D.* | N.D.* | N.D.* |
| Acetaldehyde | N.D.* | N.D.* | N.D.* |

N.D.* = Not detected

Results demonstrate that there were no detectable levels of conventional e-cigarette toxins in the vapour of the formulation, irrespective of mode of delivery, suggesting that the formulation of the present invention shows a reduction in the formation of deleterious by-products, at both ambient and conventional e-cigarette temperatures.

All of the features disclosed in this specification (including any accompanying claims, abstract and drawings), and/or all of the steps of any method or process so disclosed, may be combined in any combination, except combinations where at least some of such features and/or steps are mutually exclusive. Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features. The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. A liquid pharmaceutical formulation, comprising:
   0.1-8% wt. % of nicotine;
   at least 65 wt. % water; and
   one or more of flavouring agents, co-solubilisers and solubilisers;
   wherein the formulation comprises a co-solubiliser and/or a solubiliser;
   wherein the nicotine is the form of a nicotine salt of nicotine and an acid;
   wherein the acid is selected from lactic acid, 2-methylpropanoic acid, acetylsalicylic acid, 2-aminoethanesulfonic acid (taurine), aminomethylphosphonic acid, arachidic acid, ascorbic acid, azelaic acid, barbituric acid, benzoic acid, benzylic acid, butanoic acid, capric acid, caproic acid, caprylic acid, carbonic acid, cinnamic acid, decanoic acid, dodecanoic acid, enanthic acid, ethanoic acid, folic acid, fumaric acid, gluconic acid, glutaric acid, heptanoic acid, hexanoic acid, icosanoic acid, ketobutyric acid, maleic acid, malonic acid, margaric acid, methanoic acid, 3,7-dimethyl-6-octenoic acid, myristic acid, nonadecanoic acid, nonadeclylic acid, ocatadecanoic acid, octanoic acid, oleic acid, 2-oxobutyric acid, pelargonic acid, pentadecanoic acid, pentadecylic acid, pentanoic acid, propanoic acid, propiolic acid, quinic acid, rosolic acid, stearic acid and succinic acid, tetradecanoic acid, p-toluenesulfonic acid, tridecanoic acid, tridecylic acid, trifluoroacetic acid, trifluoromethanesulfonic acid, undecanoic acid, undecylic acid and uric acid;
   wherein the pharmaceutical formulation has a pH of from 4.5 to 5.9;
   wherein the formulation does not include a separate buffering agent or pH regulating agent; and
   wherein the liquid pharmaceutical formulation is aerosolisable to form an inhalable formulation.

2. A pharmaceutical formulation as claimed in claim 1, comprising at least 75% water.

3. A pharmaceutical formulation as claimed in claim 1, wherein the formulation is in the form of aerosolised droplets.

4. A pharmaceutical formulation as claimed in claim 1, wherein:
   (i) the formulation comprises a flavouring agent, optionally wherein the flavouring agent is a tobacco, mint or fruit flavouring; and/or
   (ii) wherein the formulation additionally comprises a sweetener.

5. A pharmaceutical formulation as claimed in claim 1, wherein the formulation comprises a co-solubiliser selected from propylene glycol, polyethylene glycol, glycerine, polyethylene glycol/polypropylene glycol co-polymers, polyvinylpyrrolidone, 1,2-hexanediol, 1,2-pentanediol, diethylene glycol mono ethyl ether, dimethyl isosorbide, ethanol, n-Butanol n-Pentanol, and mixtures thereof.

6. A pharmaceutical formulation as claimed claim 1, wherein the formulation comprises a solubiliser selected from polyoxyethylene (40) castor oil, poly(ethylene glycol)-block-poly(propylene glycol)-block-poly(ethylene glycol), polyoxyl (35) castor oil, polyoxyl (40) castor oil, polyoxyl (40) castor oil in admixture with PPG-1-PEG 9 lauryl glycol ether, PPG-1-PEG 9 lauryl glycol ether, polyoxyethylated 12-hydroxystearic acid, PEG 300, PEG 400, dioleic acid PEG 600 ester, heptyl glucoside, isostearic acid monoisopropanolamide, coconut fatty acid diethanolamide, coconut fatty acid glycol ester, coconut fatty acid monoethanolamide, coconut fatty acid PEG200 ester, coconut fatty acid PEG600 ester, oleic acid PEG600 ester, oleic acid C12-C14 alkylester, oleic acid diethanolamide, oleic acid monoisopropanolamide, oleic acid PEG1000 ester, oleic acid PEG200 ester, rape seed oil diethanolamide, tall oil fatty acid diethanolamide, tall oil fatty acid monoisopropanolamide, tall oil PEG200 ester, tall oil PEG600 ester, polysorbate 20, polysorbate 40 (polyoxyethylene sorbitan monopalmitate, polysorbate 60, polysorbate 65, polysorbate 80, polysorbate 85, sorbitan monolaurate, sorbitan monopalmitate, sorbitan monostearate, sorbitan monooleate, sorbitan monoisostearate, sorbitan tristearate, C12-C13 Pareth 9 and mixtures thereof.

7. A pharmaceutical formulation as claimed in claim 1, the formulation comprising:
- from 75 to 85 wt. % water;
- from 0.1 to 8 wt. % nicotine;
- from 0.1 to 15 wt. % co-solubiliser;
- from 0.5 to 1.5 wt. % sweetener;
- from 0.05 to 1.5 wt. % of flavouring.

8. A method of delivering nicotine to a subject, comprising:
providing an aerosolised formulation comprising 0.1-8% wt. % of nicotine; at least 65 wt % water; and one or more of flavouring agents, co-solubilisers and solubilisers;
wherein the formulation comprises a co-solubiliser and/or a solubiliser;
wherein the nicotine is the form of a nicotine salt of nicotine and an acid, wherein the acid is selected from lactic acid, 2-methylpropanoic acid, acetylsalicylic acid, 2-aminoethanesulfonic acid (taurine), aminomethylphosphonic acid, arachidic acid, ascorbic acid, azelaic acid, barbituric acid, benzoic acid, benzylic acid, butanoic acid, capric acid, caproic acid, caprylic acid, carbonic acid, cinnamic acid, decanoic acid, dodecanoic acid, enanthic acid, ethanoic acid, folic acid, fumaric acid, gluconic acid, glutaric acid, heptanoic acid, hexanoic acid, icosanoic acid, ketobutyric acid, maleic acid, malonic acid, margaric acid, methanoic acid, 3,7-dimethyl-6-octenoic acid, myristic acid, nonadecanoic acid, nonadeclylic acid, ocatadecanoic acid, octanoic acid, oleic acid, 2-oxobutyric acid, pelargonic acid, pentadecanoic acid, pentadecylic acid, pentanoic acid, propanoic acid, propiolic acid, quinic acid, rosolic acid, stearic acid and succinic acid, tetradecanoic acid, p-toluenesulfonic acid, tridecanoic acid, tridecylic acid, trifluoroacetic acid, trifluoromethanesulfonic acid, undecanoic acid, undecylic acid and uric acid;
wherein the formulation does not include a separate buffering agent or pH regulating agent;
and wherein the pharmaceutical formulation has a pH of from 4.5 to 5.9;

and administering the aerosolised formulation via inhalation.

9. A method of delivering nicotine to a subject as claimed in claim 8, wherein the method further comprises providing a liquid formulation comprising 0.1-8% wt. % of nicotine and at least 65 wt. % water; and nebulising the liquid formulation to form the aerosolised formulation; optionally wherein the liquid formulation is nebulised via the application of oxygen, compressed air or ultrasonic power to form the aerosolised formulation.

10. A cartridge for use with an e-cigarette, wherein the cartridge comprises the formulation according to claim 1.

11. An e-cigarette comprising a cartridge as claimed in claim 10.

12. A pharmaceutical formulation as claimed in claim 1, wherein the acid is lactic acid.

13. A pharmaceutical formulation as claimed in claim 5, wherein the co-solubiliser is propylene glycol, glycerine, or a mixture thereof.

* * * * *